(12) United States Patent
Johnson et al.

(10) Patent No.: US 7,964,595 B2
(45) Date of Patent: Jun. 21, 2011

(54) THIOPHENYL PROSTAGLANDIN DERIVATIVES FOR TREATING GLAUCOMA AND OCULAR HYPERTENSION

(75) Inventors: Brent A. Johnson, Rancho Santa Margarita, CA (US); David W.. Old, Irvine, CA (US); Yariv Donde, Dana Point, CA (US); Robert M. Burk, Laguna Beach, CA (US)

(73) Assignee: Allergan, Inc., Irvine, CA (US)

( * ) Notice: Subject to any disclaimer, the term of this patent is extended or adjusted under 35 U.S.C. 154(b) by 79 days.

(21) Appl. No.: 12/352,995

(22) Filed: Jan. 13, 2009

(65) Prior Publication Data
US 2009/0186885 A1  Jul. 23, 2009

Related U.S. Application Data

(60) Provisional application No. 61/022,282, filed on Jan. 18, 2008.

(51) Int. Cl.
*A61K 31/535* (2006.01)
(52) U.S. Cl. ........ 514/231.5; 514/448; 549/71; 544/146
(58) Field of Classification Search ............... 514/231.5, 514/448; 549/71; 544/146
See application file for complete search history.

(56) References Cited

U.S. PATENT DOCUMENTS
| | | | |
|---|---|---|---|
| 6,586,463 B2 * | 7/2003 | deLong et al. | 514/443 |
| 2005/0209337 A1 | 9/2005 | Gutman | |

FOREIGN PATENT DOCUMENTS
| | | | |
|---|---|---|---|
| WO | WO 97/30710 | | 8/1997 |
| WO | WO 00/51977 | * | 2/2000 |
| WO | WO 02 096868 | | 12/2002 |
| WO | WO 2006/022966 | * | 3/2006 |

OTHER PUBLICATIONS

Carey, Francis A.: Organic Chemistry, New York: McGraw-Hill Book Company 1987, p. 63.
Smith and March, March's Advanced Organic Chemistry, 5$^{th}$ Ed., New York: Wiley-Interscience, 2001, pp. 1195-1196.
U.S. Appl. No. 60/805,285, filed Jul. 20, 2006, Old.

\* cited by examiner

*Primary Examiner* — Yong Chu
*Assistant Examiner* — Valerie Rodriguez-Garcia
(74) *Attorney, Agent, or Firm* — Kevin J. Forrestal; John E. Wurst; Doina G. Ene

(57) ABSTRACT

Disclosed herein is a compound according to one of the formulas

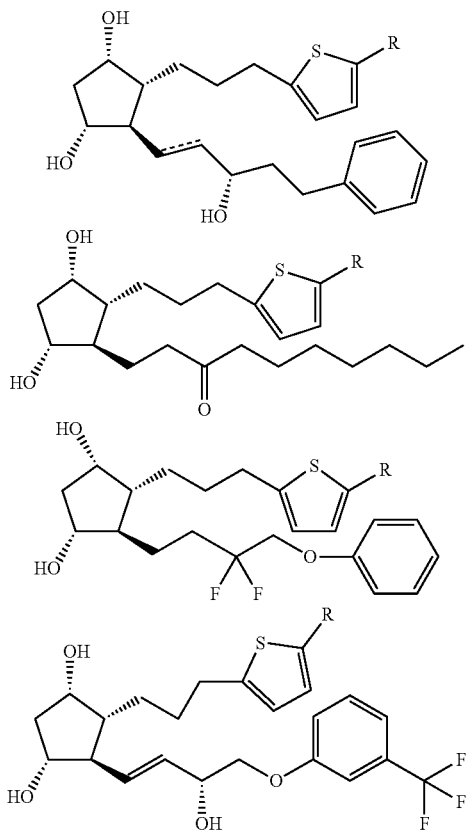

wherein R is

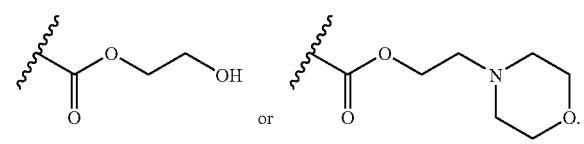

Additionally, pharmaceutically acceptable salt thereof, and methods of treating disease, medicaments, and compositions related thereto, are further elaborated herein.

13 Claims, No Drawings

THIOPHENYL PROSTAGLANDIN DERIVATIVES FOR TREATING GLAUCOMA AND OCULAR HYPERTENSION

CROSS-REFERENCE TO RELATED APPLICATION

This application is based, and claims priority under 35 U.S.C. § 120 to U.S. Provisional Patent Application No. 61/022,282 filed on Jan. 18, 2008, and which is incorporated herein by reference.

BACKGROUND

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from preexisting ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

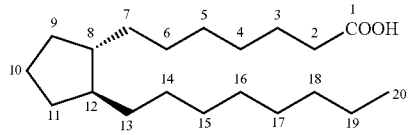

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

SUMMARY

Disclosed herein are compounds useful in treating glaucoma and stimulating hair growth. Compounds disclosed herein are also useful in stimulating the conversion of vellus hair to terminal hair. In one embodiment, the compounds described herein have one of the formulas:

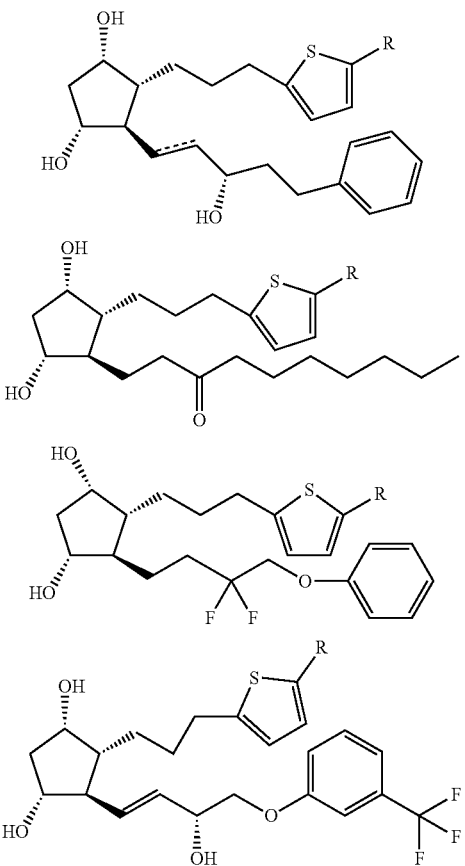

or a pharmaceutically acceptable salt thereof, wherein a dashed line represents the presence or absence of a bond; wherein R is

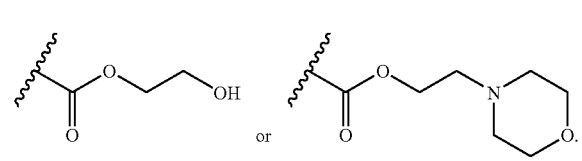

DETAILED DESCRIPTION

Disclosed herein is a compound according to one of the formulas

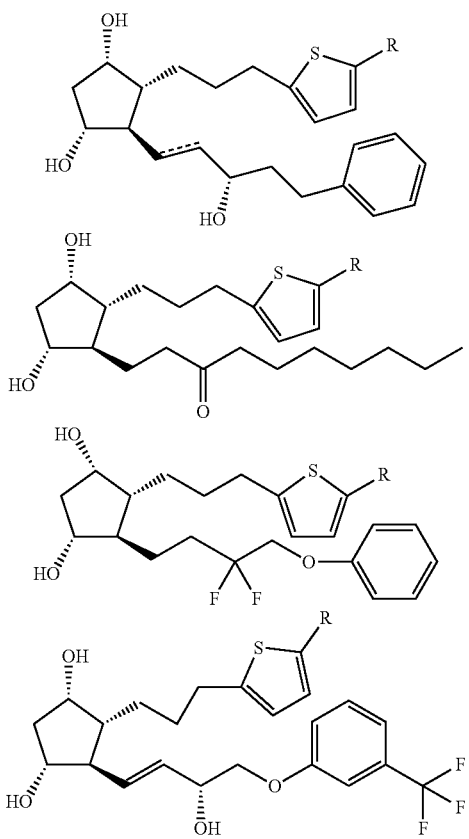

or a pharmaceutically acceptable salt thereof
wherein a dashed line represents the presence or absence of a double bond;

wherein R is A pharmaceutically acceptable salt is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt. Examples of useful salts include, but are not limited to, sodium salts, potassium salts, calcium salts, ammonium salts and the like.

A person of ordinary skill in the art understands the meaning of the stereochemistry associated with the hatched wedge/solid wedge structural features. For example, an introductory organic chemistry textbook (Francis A. Carey, Organic Chemistry, New York: McGraw-Hill Book Company 1987, p. 63) states "a wedge indicates a bond coming from the plane of the paper toward the viewer" and the hatched wedge "represents a bond receding from the viewer."

For the purposes of this disclosure, "treat," "treating," or "treatment" refer to the use of a compound, composition, therapeutically active agent, or drug in the diagnosis, cure, mitigation, treatment, or prevention of disease or other undesirable condition.

One embodiment is a composition comprising a compound disclosed herein, wherein said composition is a liquid which is ophthalmically acceptable.

Another embodiment is use of a compound disclosed herein in the manufacture of a medicament for the treatment of glaucoma or ocular hypertension in a mammal.

Another embodiment is use of a compound disclosed herein in the manufacture of a medicament for the stimulation of hair growth in mammals.

Another embodiment is use of a compound disclosed herein in the manufacture of a medicament for the stimulation of the conversion of vellus hair to terminal hair.

Another embodiment is a medicament comprising a compound disclosed herein, wherein said composition is a liquid which is ophthalmically acceptable.

Another embodiment is a method comprising administering a compound disclosed herein to a mammal for the treatment of glaucoma or ocular hypertension.

Another embodiment is a kit comprising a composition comprising compound disclosed herein, a container, and instructions for administration of said composition to a mammal for the treatment of glaucoma or ocular hypertension.

Another embodiment is a method comprising administering a compound disclosed herein to a mammal for the stimulation of hair growth in mammals.

Another embodiment is a method comprising administering a compound disclosed herein to a mammal for the stimulation of the conversion of vellus hair to terminal hair.

Scheme 1

Synthetic Methods

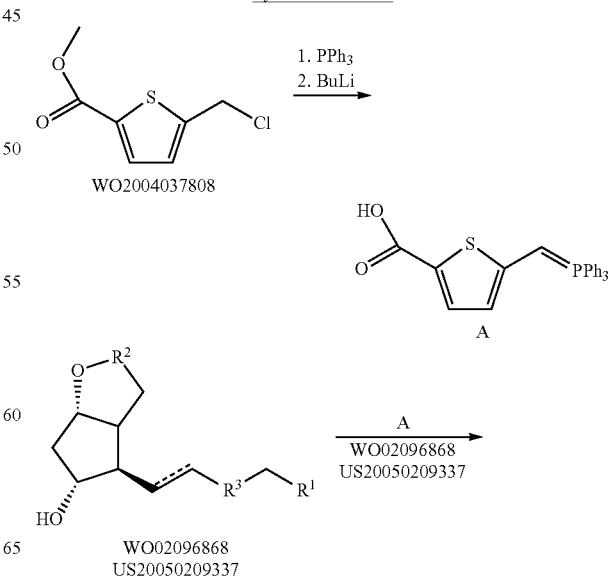

-continued

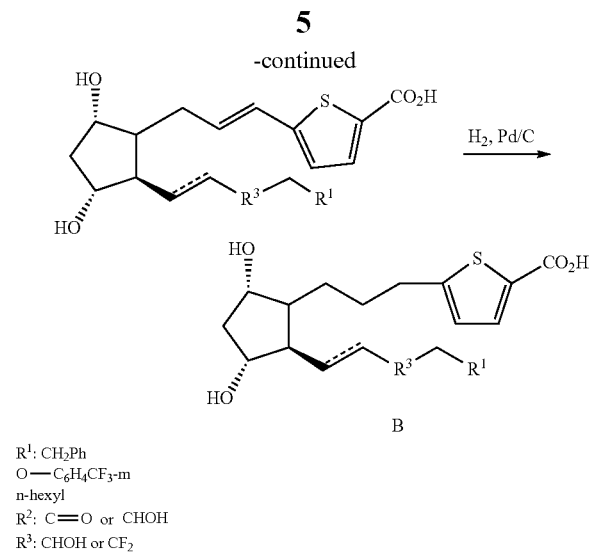

B

R$^1$: CH$_2$Ph
O—C$_6$H$_4$CF$_3$-m
n-hexyl
R$^2$: C═O or CHOH
R$^3$: CHOH or CF$_2$ A person of ordinary skill in the art recognizes that are many potential methods to prepare these compounds. For example, WO02096868 and US20050209337 disclose methods that can be adapted to prepare these compounds (Scheme 1). A thienyl containing Wittig reagent (A) can be substituted for the linear Wiffig reagent of those reference to yield the thienyl containing alpha chain. The resulting thienyl propenyl thienyl alpha chain can then be hydrogenated to yield the desired alpha chain. The terminal ester can then be converted according to the following.

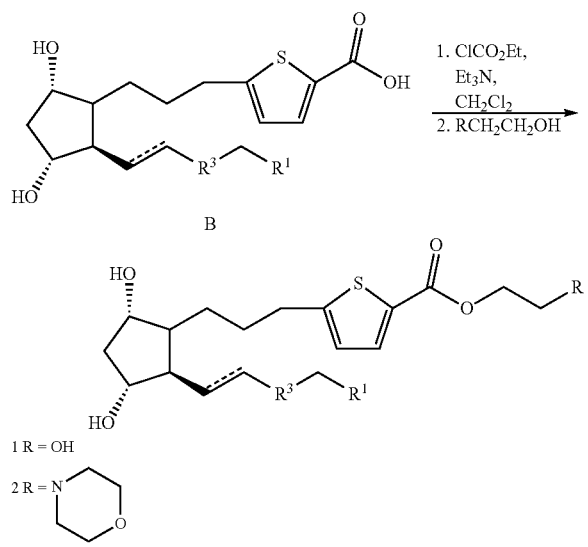

Compound 1 can be synthesized adding triethylamine with ethyl chloroformate to a solution of Compound B in CH$_2$Cl$_2$ at room temperature. After 2.5 h, triethyl amine and ethylene glycol are added. The mixture is stirred overnight. Thereafter, the solution is partitioned between H$_2$O and CH$_2$Cl$_2$. The phases are separated and the aqueous phase is extracted with CH$_2$Cl$_2$. The combined organic phase is washed with HCl the dried, filtered and concentrated. Purification of the residue by flash column chromatography on silica gel affords Compound 1.

Compound 2 can be synthesized adding triethylamine with ethyl chloroformate to a solution of Compound B in CH$_2$Cl$_2$ at room temperature. After 2.5 h, triethyl amine and 4-(2-hydroxyethyl)-morpholine are added. The mixture is stirred overnight. Thereafter, the solution is partitioned between H$_2$O and CH$_2$Cl$_2$. The phases are separated and the aqueous phase is extracted with CH$_2$Cl$_2$. The combined organic phase is washed with HCl the dried, filtered and concentrated. Purification of the residue by flash column chromatography on silica gel affords Compound 2.

Compound A may also be substituted with a compound such as Compound B, and the alpha chain can be attached as described in U.S. Provisional Patent Application No. 60/805, 285, filed on Jul. 20, 2006.

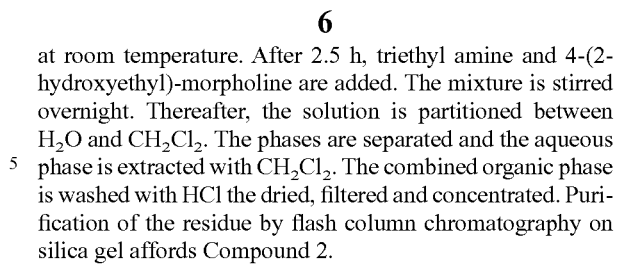

B

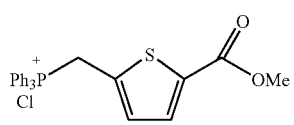

Scheme 2

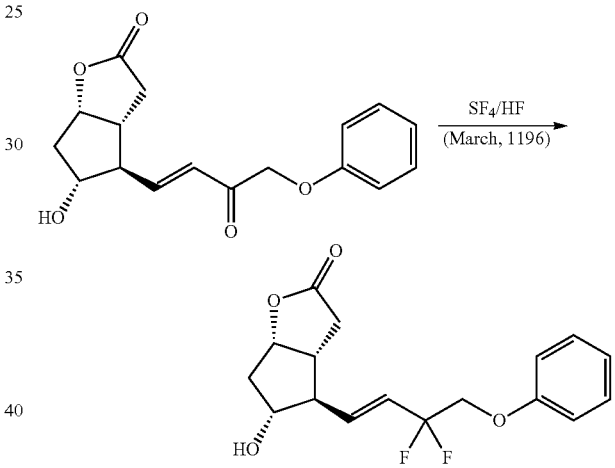

Compounds having CF$_2$ for R$^3$ may be prepared by reaction with SF4/HF or an equivalent reagent as described in Smith and March, March's Advanced Organic Chemistry, Fifth Ed., New York: Wiley-Interscience, 2001, pp. 1195-1196. Other methods may also be used.

Formulation Methods

Ophthalmic Applications

A liquid which is ophthalmically acceptable is formulated such that it can be administered topically to the eye. The comfort should be maximized as much as feasible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used to achieve an ophthalmically acceptable pH. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjuster | 1-10 |
| buffer | 0.01-10 |
| pH adjuster | q.s. pH 4.5-7.5 |
| antioxidant | as needed |
| surfactant | as needed |
| purified water | as needed to make 100% |

The actual dose of the active compounds depends on the specific compound, and on the condition to be treated; the selection of the appropriate dose is well within the knowledge of the skilled artisan.

Applications for Stimulating Hair Growth

In one embodiment, the compounds disclosed herein can be useful in the treatment of baldness and/or hair loss. Alopecia (baldness) is a deficiency of either normal or abnormal hair, and is primarily a cosmetic problem in humans. It is a deficiency of terminal hair, the broad diameter, colored hair that is readily seen. However, in the so called bald person, although there is a noticeable absence of terminal hair, the skin does contain vellus hair, which is a fine colorless hair which may require microscopic examination to determine its presence. This vellus hair is a precursor to terminal hair.

The compounds described herein can be used to stimulate, such as the conversion of vellus hair to growth as terminal hair, as well as increasing the rate of growth of terminal hair. The utility of the compounds described herein for the simulation of hair growth was discovered as follows.

In the course of treating patients having glaucoma, treatment may only be appropriate in one eye. Within the course of daily practice, it was discovered that a patient who had been treated with bimatoprost, a prostaglandin analogue, developed lashed that were longer, thicker, and fuller in the treated eye than in the non-treated eye. On examination, the difference was found to be very striking. The lashes were longer and had a fuller, denser appearance in the treated eye. The lash appearance on the lids of the treated eyes would have appeared quite attractive if it represented a bilateral phenomenon. As a result of its asymmetric nature, the long lashes on one side could be construed as disturbing from a cosmetic standpoint. A systemic examination was preformed as a result of the asymmetric phenomenon. It soon became apparent that this altered appearance was not an isolated finding. Comparison of the lids of patients who were taking bimatoprost in only one eye revealed subtle changes in the lashed and adjacent hairs of the bimatoprost-treated side in several patients. Definite differences could be identified to varying degrees in the lashes and adjacent hairs of all patients who were taking the drug on a unilateral basis for longer than 6 months.

The changes in the lashes were apparent on gross inspection in several patients once attention was focused on the issue. In those with light colored hair and lashes, the differences were only seen easily with the aid of the high magnification and lighting capabilities of the slit lamp biomicroscope. In the course of glaucoma follow-up examination, attention is generally immediately focused on the eye itself. As a result of the high power magnification needed only one eye is seen at a time and the eye is seen at a high enough power that the lashes are not in focus. At these higher powers, any lash asymmetry between the two eyes is not likely to be noticed except by careful systematic comparison of the lashes and adjacent hairs of the eyelids of the two eyes.

Observed parameters leading to the conclusion that more robust hair growth occurred in the treatment area following administration of the prostaglandin analogue were multiple. They included increased length of lashed, increased number of lashes along the normal lash line, increased thickness and luster of lashes, increased auxiliary lash-like terminal hair in transitional areas adjacent to areas of normal lash growth, increased auxiliary lash-like terminal hairs at the medial and lateral canthal area, increased pigmentation of the lashes, increased numbers, increased length, as well as increased luster, and thickness of fine hair on the skin of the adjacent lid, and finally, increased perpendicular angulation of lashes and lash-like terminal hairs. The conclusion that hair growth is stimulated by prostaglandin analogues such as bimatoprost is thus supported not by evidence of a difference in a single parameter, but is based on multiple parameters of hair appearance in treated versus control areas in many subjects.

The compounds described herein are prostaglandin analogues and therefore have similar activities as bimatoprost, contain structural similarities, and therefore are expected to stimulate hair growth and stimulation of the conversion of vellus hair to terminal hair. In one embodiment, the compounds described herein and their prodrugs can be used for the stimulation of hair growth. As used herein, hair growth includes hair associated with the scalp, eyebrows, eyelids, beard, and other areas of the skin of animals.

In one embodiment, the compound is mixed with a dermatologically compatible vehicle or carrier. The vehicle, which may be employed for preparing compositions as described herein, may comprise, for example, aqueous solutions such as e.g., physiological salines, oil solutions, or ointments. The vehicle furthermore may contain dermatologically compatible preservatives such as e.g., benzalkonium chloride, surfactants like e.g., polysorbate 80, liposomes or polymers, for example, methyl cellulose, polyvinyl alcohol, polyvinyl pyrrolidone and hyaluronic acid; these may be used for increasing the viscosity. Furthermore, it is also possible to use soluble or insoluble drug inserts when the drug is to be administered.

In one embodiment, dermatological compositions can be formulated for topical treatment for the stimulation of hair growth which comprises an effective hair growth simulating amount of one or more compounds as defined above and a dermatologically compatible carrier. Effective amounts of the active compounds may be determined by one of ordinary skill in the art, but will vary depending on the compound employed, frequency of application and desired result. The compound will generally range from about 0.0000001 to about 50% by weight of the dermatological composition. Preferably, the compound will range from about 0.001 to about 50% by weight of total dermatological composition, more preferably from about 0.1 to about 30% by weight of the composition.

In one embodiment, the application of the present compounds for stimulation of hair growth finds applications in mammalian species, including both humans and animals. In humans, the compounds described herein can be applied for example, to the scalp, face beard, head, pubic area, upper lip, eyebrows, and eyelids. In animal raised for their pelts, e.g., mink, the compounds described herein can be applied over the entire surface of the body to improve the overall pelt for commercial reasons. The process can also be used for cosmetic reasons in animals, e.g., applied to the skin of dogs and cats having bald patches due to mange or other diseases causing a degree of alopecia.

The pharmaceutical compositions contemplated for the stimulation of hair growth include pharmaceutical compositions suited for topical and local action. The term "topical" as employed herein relates to the use of a compound, as described herein, incorporated in a suitable pharmaceutical carrier, and applied at the site of thinning hair or baldness for exertion of local action. Accordingly, such topical compositions include those pharmaceutical forms in which the compound is applied externally by direct contact with the skin to be treated. Conventional pharmaceutical forms for this purpose include ointments, liniments, creams, shampoos, lotions, pastes, jellies, sprays, aerosols, and the like, and may be applied in patches or impregnated dressings depending on the part of the body to be treated. The term "ointment" embraces formulations (including creams) having oleaginous, water-soluble and emulsion-type bases, e.g., petrolatum, lanolin, polyethylene glycols, as well as mixtures of these.

Typically, the compounds can be applied repeatedly for the sustained period of time topically on the part of the body to be treated, for example, the eyelids, eyebrows, skin or scalp. The preferred dosage regimen will generally involve regular, such as daily, administration for a period of treatment of at least one month, more preferably at least three months, and most preferably, at least six months.

For topical use on the eyelids or eyebrows, the active compounds can be formulated in aqueous solutions, creams, ointments, or oils exhibiting physologicla acceptable osmolarity by addition of pharmaceutically acceptable buffers and salts. such formulations may or may not, depending on the dispenser, contain preservatives such as benzalkonium chloride, chlorhexidine, chlorobutanol, parahydroxybenzoic acids and phenylmercuric salts such as nitrate, chloride, acetate, and borate, or antioxidants, as well as additives like EDTA, sorbitol, boric acid and the like as additives. Furthermore, particularly aqueous solutions may contain viscosity increasing agents such as polysaccharides, e.g., methylcellulose, mucopolysaccharides, e.g., hyaluronic acid and chondroitin sulfate, or poly alcohol, e.g., polyvinylalcohol. Various slow releasing gels and matricies may also be employed as well as soluble and insoluble ocular inserts, for instance, based on substances forming in situ gels. Depending on the actual formation and compound to be used, various amounts of the drug and different dose regimens may be employed. Typically, the daily amount of compound for treatment of the eyelid may be about 0.1 ng to about 100 mg per eyelid.

For topical use on the skin and scalp, the compound can be advantageously formulated using ointments, creams, liniments or patches as a carrier of the active ingredient. Also, these formulations may or may not contain preservatives, depending on the dispenser and nature of use. Such preservatives include those mentioned above, and methyl-, propyl-, or butyl-parahydroxybenzoic acid, betain, chlorhexidine, benzalkonium chloride, and the like. Various matricies for the slow release delivery may also be used. Typically, the dose to be applied on the scalp is in the range of about 0.1 ng to about 100 mg per day, more preferably about 1 ng to about 10 mg per day, and most preferably about 10 ng to about 1 mg per day depending on the compound and the formulation. To achieve the daily amount of medication depending on the formulation, the compound may be administered once or several times daily with or without antioxidants.

Treatment Examples

The following are hypothetical, non-limiting examples demonstrating how a person may be treated with the compounds disclosed herein.

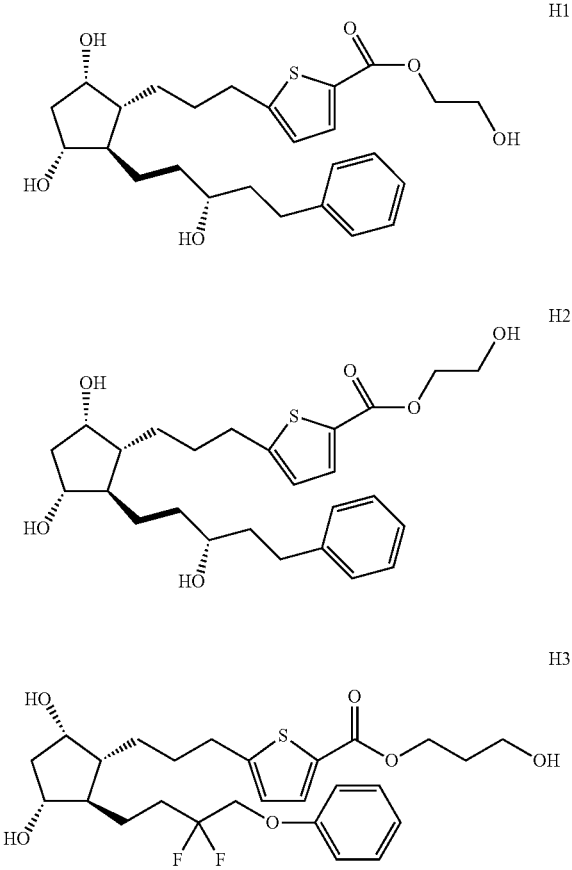

H4

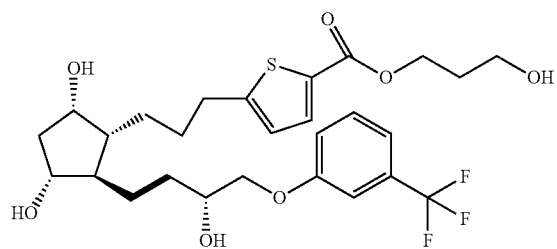

H5

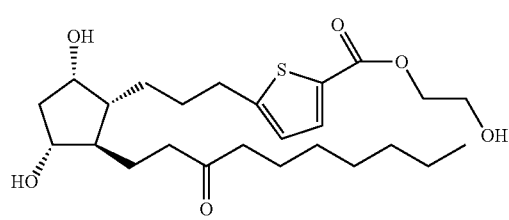

H6

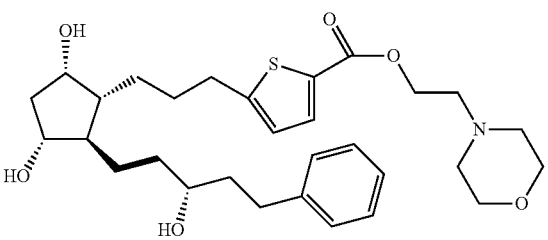

H7

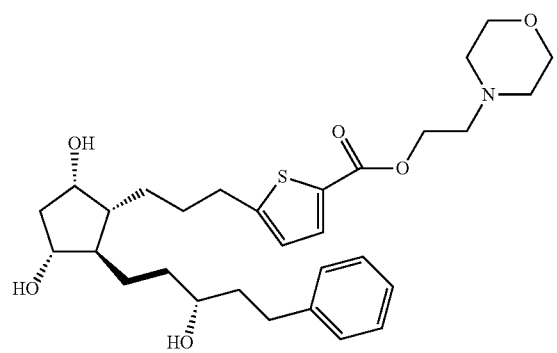

H8

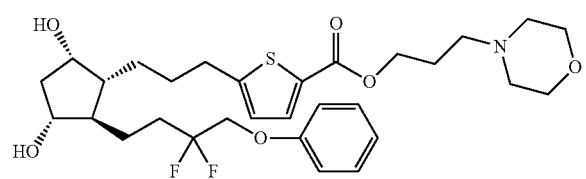

H9

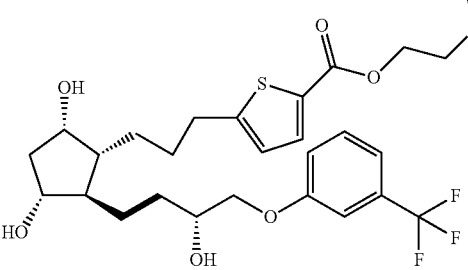

H10

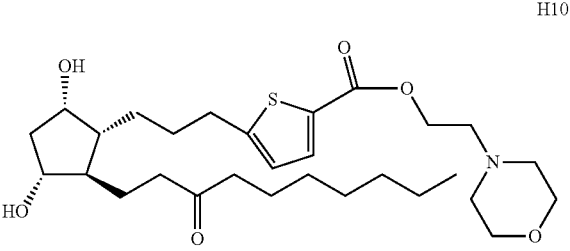

An aqueous liquid containing 0.1% of H1 is given topically to the eye of a person suffering from elevated intraocular pressure. A few hours after administration, the person's intraocular pressure is reduced. The drop is administered twice a day, and pressure remains low for as long as the treatment is continued.

An aqueous liquid containing 0.1% of H2 is given topically to the eye of a person suffering from elevated intraocular pressure. A few hours after administration, the person's intraocular pressure is reduced. The drop is administered twice a day, and pressure remains low for as long as the treatment is continued.

An aqueous liquid containing 0.1% of H3 is given topically to the eye of a person suffering from elevated intraocular pressure. A few hours after administration, the person's intraocular pressure is reduced. The drop is administered twice a day, and pressure remains low for as long as the treatment is continued.

An aqueous liquid containing 0.1% of H4 is given topically to the eye of a person suffering from elevated intraocular pressure. A few hours after administration, the person's intraocular pressure is reduced. The drop is administered twice a day, and pressure remains low for as long as the treatment is continued.

An aqueous liquid containing 0.1% of H5 is given topically to the eye of a person suffering from elevated intraocular pressure. A few hours after administration, the person's intraocular pressure is reduced. The drop is administered twice a day, and pressure remains low for as long as the treatment is continued.

An aqueous liquid containing 0.1% of H6 is given topically to the eye of a person suffering from elevated intraocular pressure. A few hours after administration, the person's intraocular pressure is reduced. The drop is administered twice a day, and pressure remains low for as long as the treatment is continued.

An aqueous liquid containing 0.1% of H7 is given topically to the eye of a person suffering from elevated intraocular pressure. A few hours after administration, the person's intraocular pressure is reduced. The drop is administered twice a day, and pressure remains low for as long as the treatment is continued.

An aqueous liquid containing 0.1% of H8 is given topically to the eye of a person suffering from elevated intraocular pressure. A few hours after administration, the person's intraocular pressure is reduced. The drop is administered twice a day, and pressure remains low for as long as the treatment is continued.

An aqueous liquid containing 0.1% of H9 is given topically to the eye of a person suffering from elevated intraocular pressure. A few hours after administration, the person's intraocular pressure is reduced. The drop is administered twice a day, and pressure remains low for as long as the treatment is continued.

An aqueous liquid containing 0.1% of H10 is given topically to the eye of a person suffering from elevated intraocular pressure. A few hours after administration, the person's intraocular pressure is reduced. The drop is administered twice a day, and pressure remains low for as long as the treatment is continued.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the claims.

In Vivo Examples

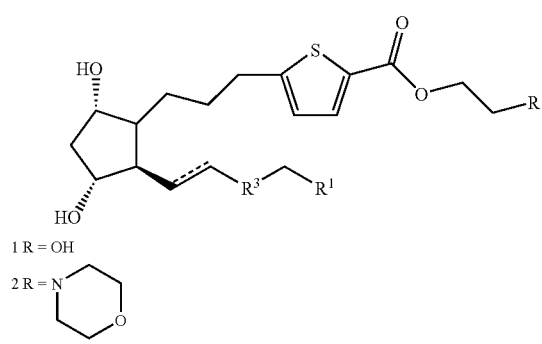

1 R = OH
2 R = N(morpholine)

Title compounds 1 and 2 from above are tested in vivo according to the following. Compound 1 is tested in normotensive dogs and the maximum intraocular pressure (IOP) decreases from baseline. This compound is also tested in laser-induced hypertensive monkeys, and a decrease in IOP from baseline is observed.

Compound 2 is tested in normotensive dogs and the maximum IOP decreases from baseline. This compound is also tested in laser-induced hypertensive monkeys, and a decrease in IOP from baseline is observed.

What is claimed is:

1. A compound according to one of the formulas

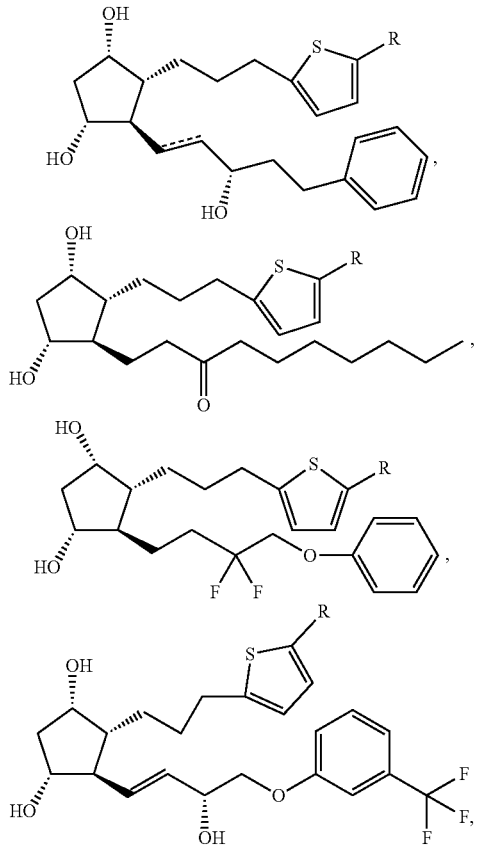

or a pharmaceutically acceptable salt thereof
wherein a dashed line represents the presence or absence of a bond; and
wherein R is

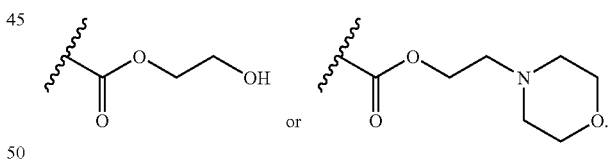

2. The compound of claim 1 of the formula

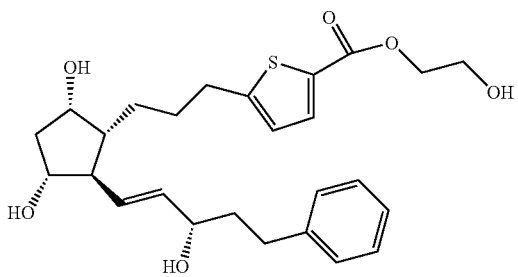

or a pharmaceutically acceptable salt thereof.

3. The compound of claim 1 of the formula

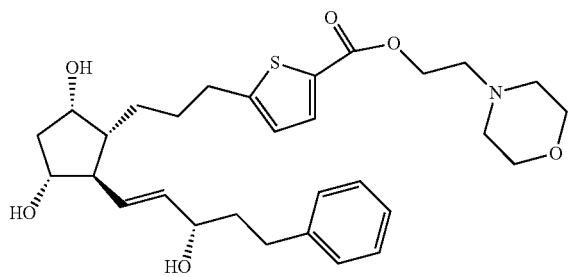

or a pharmaceutically acceptable salt thereof.

4. The compound of claim 1 of the formula

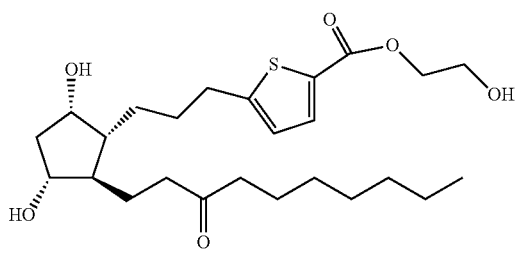

or a pharmaceutically acceptable salt thereof.

5. The compound of claim 1 of the formula

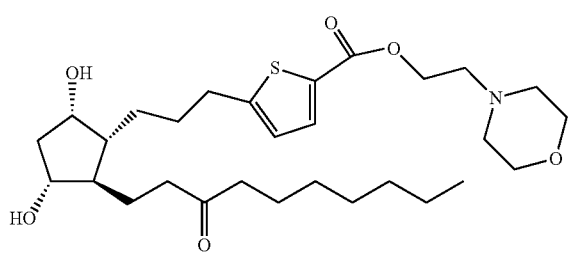

or a pharmaceutically acceptable salt thereof.

6. The compound of claim 1 of the formula

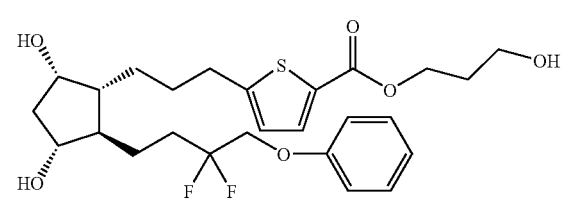

or a pharmaceutically acceptable salt thereof.

7. The compound of claim 1 of the formula

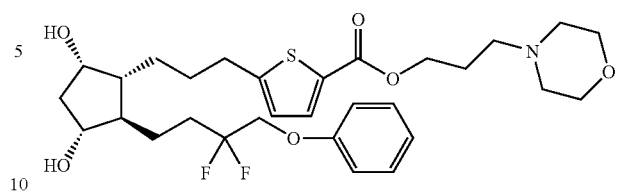

or a pharmaceutically acceptable salt thereof.

8. The compound of claim 1 of the formula

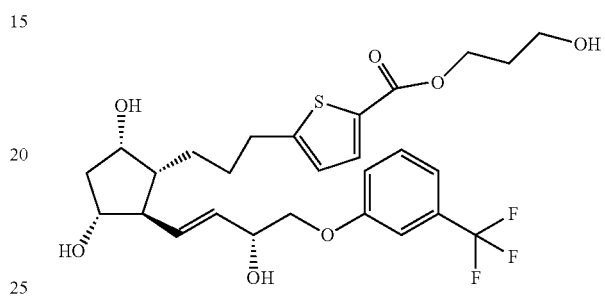

or a pharmaceutically acceptable salt thereof.

9. The compound of claim 1 of the formula

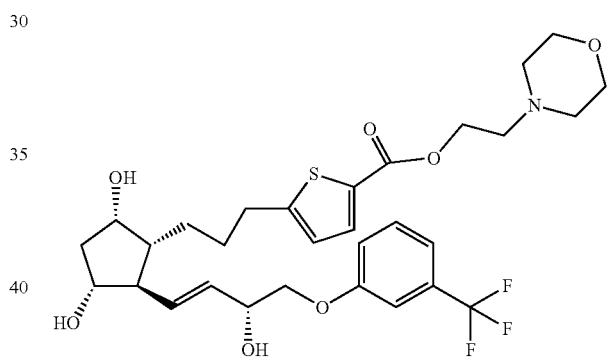

or a pharmaceutically acceptable salt thereof.

10. A method of treating glaucoma or ocular hypertension comprising administering a compound according to claim 1 wherein said treating consists of treating, mitigating or curing an established condition.

11. A composition comprising a compound according to claim 1, wherein said composition is an aqueous liquid suitable for topical ophthalmic administration.

12. A kit comprising a composition of claim 11, a package for dispensing drops of the liquid, and directions indicating use of the composition topically for treating glaucoma or ocular hypertension.

13. A method for the stimulation of hair growth comprising administering a compound according to claim 1.

\* \* \* \* \*